United States Patent
Schwarz

(10) Patent No.: US 6,400,791 B1
(45) Date of Patent: Jun. 4, 2002

(54) CT DEVICE FOR GENERATING TOMOGRAMS OF SLICES OF A SUBJECT WHICH ARE INCLINED RELATIVE TO THE LONGITUDINAL AXIS OF A PATIENT SUPPORT

(75) Inventor: Karl Schwarz, Roth (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/585,533

(22) Filed: Jun. 2, 2000

(30) Foreign Application Priority Data

Jun. 23, 1999 (DE) .......................................... 199 28 738

(51) Int. Cl.$^7$ ................................................ A61B 6/00
(52) U.S. Cl. ........................................ 378/17; 378/15
(58) Field of Search ................................ 378/4, 17, 19, 378/20, 208, 209, 15

(56) References Cited

U.S. PATENT DOCUMENTS

| 4,989,142 | A | | 1/1991 | Crawford | |
|---|---|---|---|---|---|
| 5,042,487 | A | * | 8/1991 | Marquardt | 378/17 |
| 5,357,429 | A | * | 10/1994 | Levy | 378/17 |
| 5,574,763 | A | | 11/1996 | Dehner | |
| 6,178,220 | B1 | * | 1/2001 | Freundlich et al. | 378/4 |

* cited by examiner

Primary Examiner—David P. Porta
(74) Attorney, Agent, or Firm—Schiff Hardin & Waite

(57) ABSTRACT

In a computed tomography (CT) device for generating tomograms of slices of an examination object, which are inclined relative to the longitudinal axis of a patient support plate that is provided for an examination subject, the gantry of the CT device and the support plate can be tilted relative to one another and in the tilted state, the support plate and the gantry can be linearly adjusted relative to one another substantially in the direction of the system axis of the CT device for generating a relative movement between the gantry and the support plate.

5 Claims, 4 Drawing Sheets

CT DEVICE FOR GENERATING TOMOGRAMS OF SLICES OF A SUBJECT WHICH ARE INCLINED RELATIVE TO THE LONGITUDINAL AXIS OF A PATIENT SUPPORT

BACKGROUND OF THE INVENTION

1. Field of the Invention

The present invention relates to a computed tomography (CT) device for generating tomograms of slices of an examination subject, of the type wherein the slices are inclined toward the longitudinal axis of a patient support.

2. Description of the Prior Art

In a CT device, it is necessary to be able to tilt the system axis and the longitudinal axis of the patient support relative to one another in order to be able, in the tilted state, to display objects whose center axis is inclined toward the center axis of the patient support, such as discs.

In conventional CT devices, with a detector system having a single row of detector elements, it is possible also to execute spiral scans in a tilted state, wherein the X-ray source continuously rotates around the system axis and the patient support is translationally adjusted in the direction of its longitudinal axis.

U.S. Pat. No. 5,574,763 discloses a CT device for spiral scanning of patients in an upright posture, whereby, instead of a movement of the patient support in the direction of its longitudinal axis, a relative movement of gantry and patient support is generated by vertically moving the gantry and by horizontally moving the patient support, so that the relative movement proceeds in the direction of the longitudinal axis of the patient support.

U.S. Pat. No. 4,989,142 discloses a method for acquiring data which are necessary for displaying three-dimensional surfaces, from tomograms of slices that are inclined toward the system axis, wherein these tomograms are picked up by a conventional CT device.

Spiral scans in a tilted state are problematic with respect to newer CT devices having a detector system with a number of rows of detector elements. These problems are based on arise because methods which are normally used in the course of the image reconstruction for the spiral interpolation, are not utilizable for the tilted state of the CT device and, moreover, complicated methods for the spiral interpolation are necessary, which serve the purpose of calculating an image of a single slice from data acquired during a spiral scan. Problems also arise because conventional methods are not utilizable for eliminating ring artefacts in the tomograms acquired in the tilted state.

SUMMARY OF THE INVENTION

An object of the present invention is to provide a CT device of the type initially described wherein conventional methods can be utilized for the spiral interpolation and for eliminating ring artefacts, even though a detector system having a number of rows of detector elements is used.

According to the invention, this object is achieved in a computed tomography (CT) device for generating tomograms of slices of the examination subject, the slices being inclined toward the longitudinal axis of a patient support for an examination subject, wherein the CT device has an X-ray source, which can be displaced around a system axis, and a detector system with a number of rows of detector elements, the X-ray source and the detector system being mounted at a gantry, wherein the gantry and the patient support can be tilted relative to one another such that the system axis and the longitudinal axis of the patient support are inclined relative to one another in the tilted state, and wherein, in the tilted state, the patient support and the gantry can be substantially linearly adjusted relative to one another in the direction of the system axis for generating a relative movement between the gantry and the patient support.

In contrast to conventional devices, the relative movement between the gantry and the patient support does not ensue in the direction of the longitudinal axis of the patient support but, instead ensues in the direction of the system axis. It is thus possible to utilize known methods for the spiral interpolation and for eliminating ring artefacts, although the CT device is operated in the tilted condition.

In a version of the invention the system axis extends substantially horizontally in the tilted state. In this case, tilting of the gantry can be foregone, since the longitudinal axis of the patient support assumes a direction that is inclined relative to the horizontal, however, such a position of the patient support can be somewhat uncomfortable for patients.

In another version of the invention the longitudinal axis of the patient support extends substantially horizontal in the tilted state. In this case, an inclination of the patient support that may be unpleasant for the patients is avoided, however, appropriate actions must be taken, so that a relative movement between the patient support and the gantry can be executed in the direction of the system axis, given a horizontally oriented longitudinal axis of the patient support.

While only one drive is necessary in the case of the horizontal arrangement of the system axis in order to effect the relative movement between the inclined patient support and the gantry in the direction of the system axis, two drives can be necessary in the case of the horizontal orientation of the longitudinal axis of the patient support. These drives make it possible, for example, to adjust the patient support in horizontal direction and the vertical direction in a synchronized fashion such that a relative movement between the gantry and patient support results in the direction of the system axis. In order to avoid the use of two drives, the patient support with a horizontally oriented support plate can be adjusted on bars that are tilted toward the horizontal to achieve a desired inclination. The support plate can be horizontally oriented by means of an adjustable piston or the like, even when different inclinations of the bars are possible.

In a preferred embodiment of the invention, in the tilted state, the patient support can be adjusted relative to the stationary gantry in the direction of the system axis for generating the relative movement between the gantry and the patient support, since an adjustment of the patient support is normally easier to carry out than an adjustment of the gantry. Adjustment of the gantry or a common adjustment of gantry and patient supports are still possible, however, in order to achieve the relative movement in the direction of the system axis.

DESCRIPTION OF THE PREFERRED EMBODIMENTS

Figure 1:
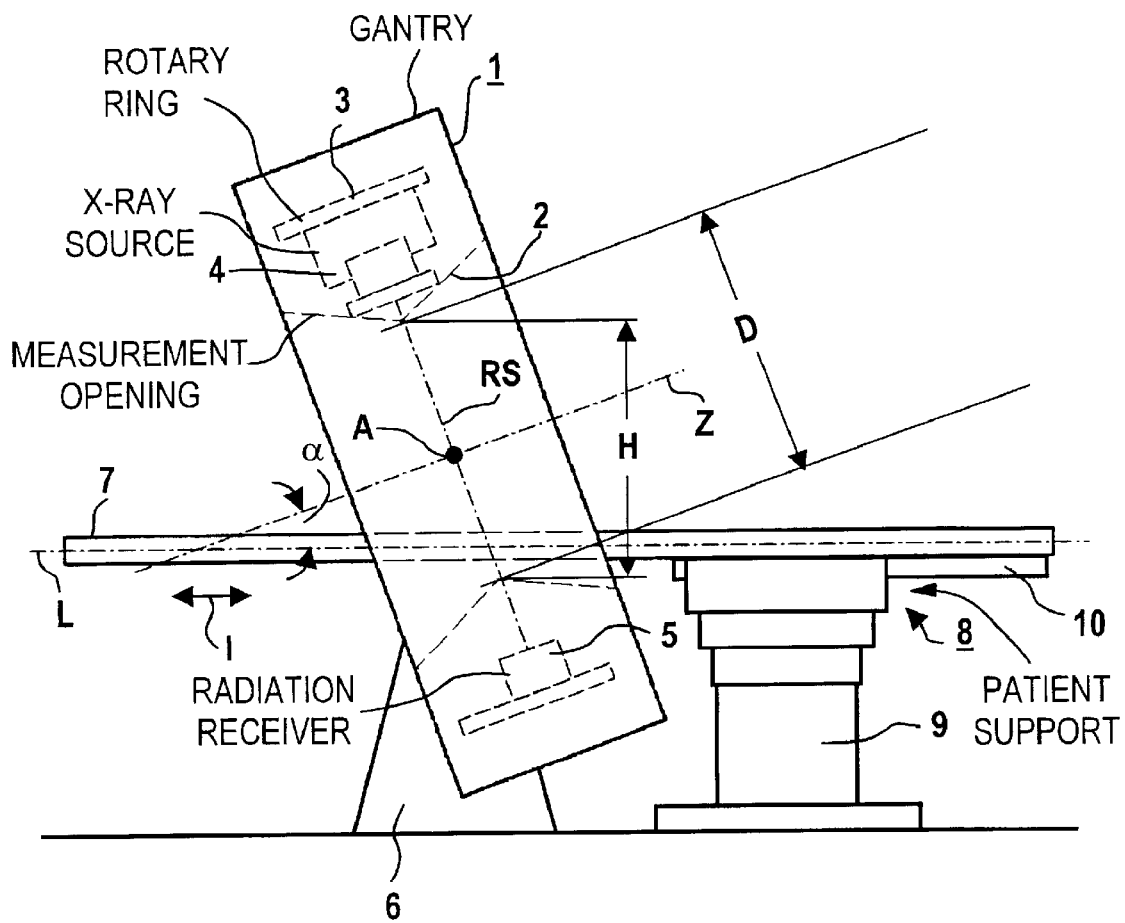
FIG. 1 shows a conventional CT device with a detector system having a single row of detector elements.

FIG. 1 shows a computed tomograph according to the state of the art, whose gantry 1 has a measuring opening 2, which is surrounded by a rotary ring 3, on which an X-ray source 4 as X-ray source and a detector system with a detector 5 are mounted. The detector 5, as is known, is curved. The X-ray source 4 emits a fan-shaped X-ray bundle RS (indicated in a dash-dotted manner from a focus), which is incident on the detector 5 that is formed of a series of detector elements and that is curved around an axis extending, preferably, parallel to a system axis Z and proceeding through the focus of the X-ray source 4.

A patient support 8 has a pedestal 9 on which a support plate 7, for accepting at least one patient is moveable along a longitudinal axis L. The gantry 1 with the X-ray source 4 and the detector 5, support plate 7, can be moved relative to one another in the direction of the longitudinal axis L of the support plate 7 by a motor-drive (not shown). In the computed tomography device according to FIG. 1, this is achieved by support plate 7 being moveably mounted to the pedestal 9 of the patient support 8, by a support element 10, so as to be adjustable in the direction of the longitudinal axis L, namely in the direction of the double arrow 1.

For preparing computed tomography images, the gantry 1 and the support plate 7 are moved relative to one another to such a position at which the support plate 7 extends through the measuring opening 2 of the gantry 1, and a patient lying on the support plate 7 assumes such a position relative to the gantry 1, so that a region of the patient to be examined is covered by the X-ray bundle RS.

For preparing an image of a planar slice of the patient, the rotary ring 3 with the X-ray source 4 and the detector 5 are rotated around the system axis Z for picking up a number of projections from different directions, which projections serve for reconstructing a tomogram of the planar slice, whereas the gantry 1 and the support plate 7 keep their positions relative to one another with respect to the direction of the system axis Z.

For performing a spiral scan, a linear relative displacement between the gantry 1 and at least the support plate 7 of the patient support 8 in the direction of the longitudinal axis L of the support plate 7, namely in the 1-direction, is undertaken with continuous rotation of the rotary ring 3, so that the picked up projections are not referenced to a planar slice but to a helix-like slice. It is possible to determine calculated projections that are referenced to a desired planar slice and that allow the reconstruction of a tomogram of this planar slice, these projections being determined from the projections that are acquired and measured in the course of the spiral scan using known methods for spiral interpolation. Besides, it is possible to eliminate ring artefacts in thus-acquired tomograms by known methods. Moreover, it is possible to reconstruct three-dimensional images on the basis of spiral scans, since not only a planar slice is scanned in the course of a spiral scan, but also a volume is scanned.

For acquiring images of planar slices, which are inclined relative to the direction of the longitudinal axis L of the support plate 7 (as it is advantageous for the imaging of discs, for example), the gantry 1 is attached to a base 6 so as to be pivotable around an axis A that is preferably horizontal and that extends transverse to the system axis Z, in a way that is not shown in greater detail and that is known (as shown in FIG. 1). The gantry 1 is tilted relative to the longitudinal axis L of the support plate 7 such that, in the tilted state, the system axis Z and the longitudinal axis L of the support plate 7 are inclined relative to one another to an extent that makes the planned examination possible.

In this tilted state, which is shown in FIG. 1, not only normal scans without relative movement between the gantry 1 and support plate 7 can be executed out, but also spiral scans can be executed, and images of good quality can be acquired on the basis of the acquired data using conventional methods.

Figure 2:
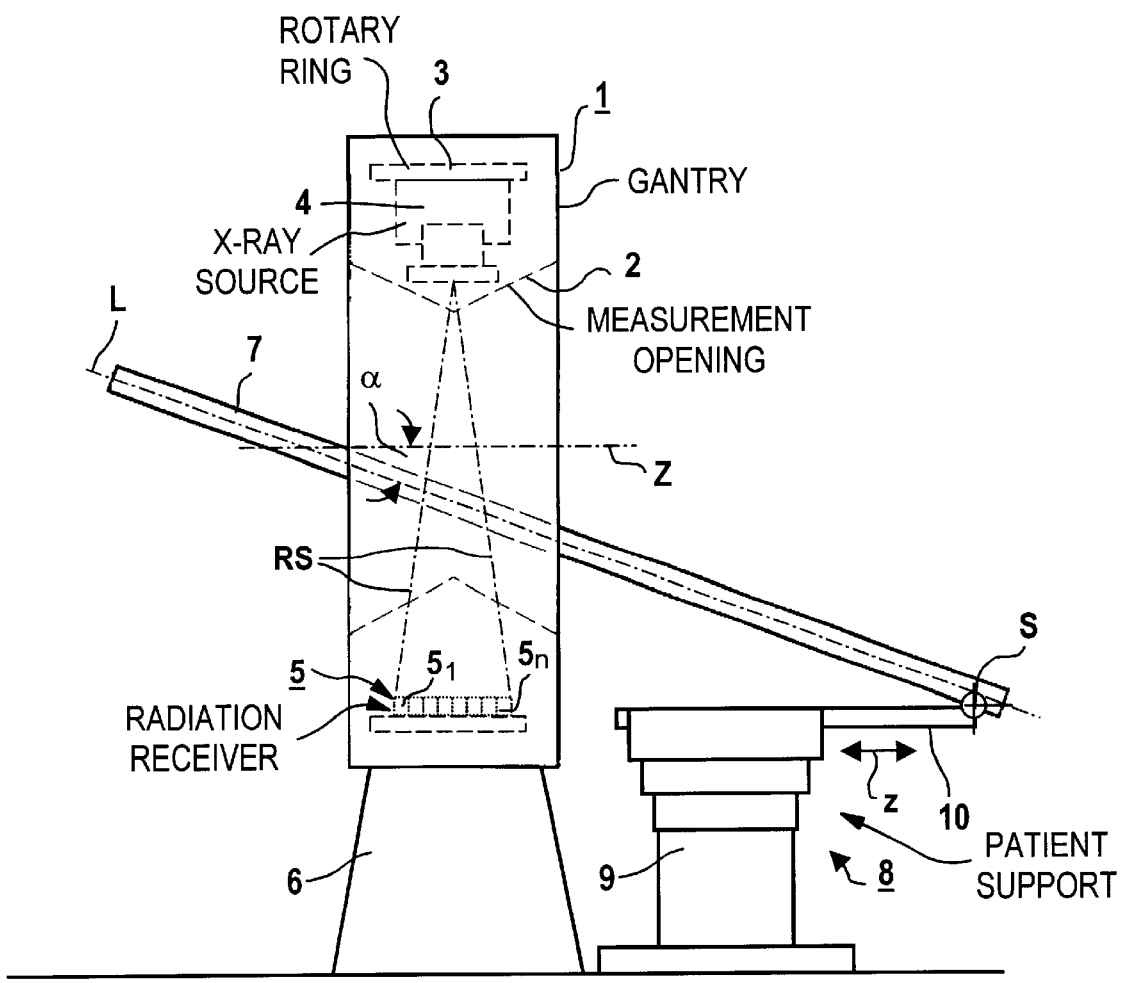
FIG. 2 shows a first embodiment of an inventive CT device with a detector system having a number of rows of detector elements.

The inventive CT device according to FIG. 2 differs from that of FIG. 1 in that the detector has a number of rows $5_1$ through $5_n$ of detector elements and in that a pyramid-shaped X-ray bundle RS is emitted by the X-ray source 4. The pyramidal X-ray bundle RS is incident on the detector 5, so that projections of slices of a patient, which slices correspond to the number of rows $5_1$ through $5_n$ of the detector 5, can be measured at the same time.

The CT device according to FIG. 2 also differs from that of FIG. 1 in that the support plate 7, by means of a motor-drive that is not shown, is pivotably mounted to the pedestal 9 of the patient support 8 around a swivelling axis S that extends transverse to the longitudinal axis L of the support plate 7. It is therefore possible, in the CT device according to FIG. 2, to place the gantry 1 and the support plate 7 relative to one another in a tilted state without pivoting the gantry 1, so that slices inclined relative to the longitudinal axis L of the support plate 7 can be imaged.

Conventional methods with the inventive CT device according to FIG. 2, given the reconstruction of images on the basis of projections acquired in the course of a spiral scan in a tilted state for the spiral interpolation and for eliminating ring artefacts can be employed in spite of the utilization of a detector 5 having a number of rows $5_1$ through $5_n$ of detector elements. This is because in accordance with the invention the linear relative movement between the gantry 1 with the X-ray source 4 and the detector 5, and the bearing plate 7, does not ensue in the direction of the longitudinal axis L of the support plate 7, which is inclined toward the system axis Z, but instead ensues in the direction of the system axis Z (as is indicated in FIG. 2 by a double arrow z); this linear relative movement being necessary for performing a spiral scan. When the gantry 1, as is the case in FIG. 2, assumes a position in which the direction of the system axis Z corresponds to the direction, in which the support part 10 can be adjusted relative to the pedestal 9 of the patient support 8 for example, the movement of the support plate 7 occurs in the direction of the system axis Z by that the support element 10, with the inclined support plate 7, being adjusted relative to the pedestal 9 in the z-direction shown by the double arrow z.

As shown in FIG. 2, with displacement of the support plate 7 in the direction of its longitudinal axis L, the projections that are acquired with the different rows $5_1$ through $5_n$ of detector elements of the detector 5 and that belong to a specific angle position of the rotary ring 3 in the gantry 1 would have to be based on rotating centers. These rotating centers would have to be respectively rectangularly measured relative to the longitudinal axis L of the support plate 7, and would have different distances from a straight line extending parallel to the direction of movement, namely to the longitudinal axis L. This means that conventional methods for the spiral interpolation and for eliminating ring artefacts cannot be used. In order to be able to employ the conventional methods for spiral interpolation and for eliminating ring artefacts, these distances must be identical; this is a condition that is fulfilled by the device of FIG. 2, since the distances of all rotating centers from a line extending parallel to the system axis Z are identical as a result of the direction of movement in the direction of the system axis Z. Therefore, conventional methods for spiral interpolation and for eliminating ring artefacts can be utilized in the inventive CT device.

Figure 3:
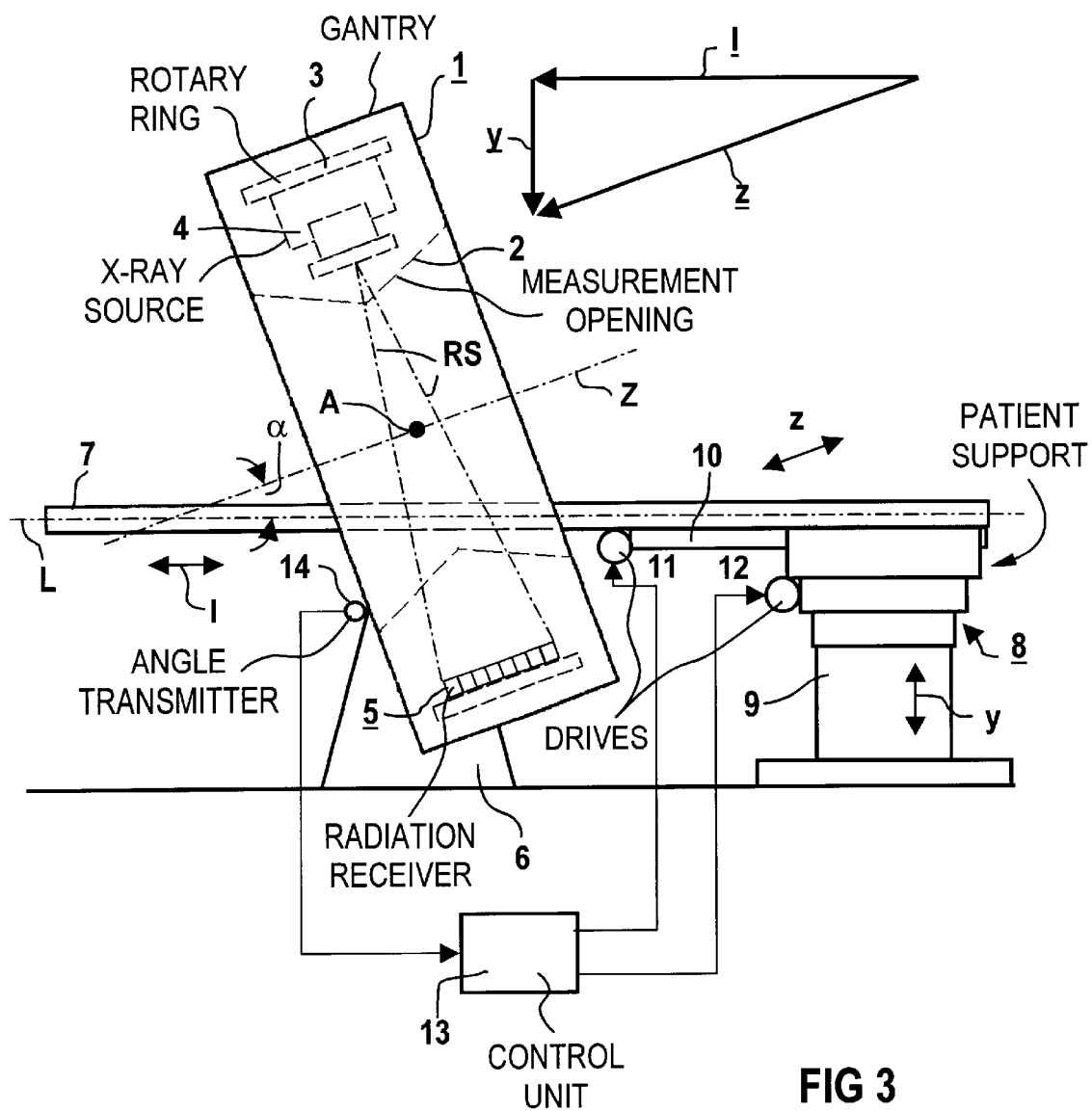
FIG. 3 shows a further version of an inventive CT device.

The exemplary embodiment according to FIG. 3 differs from that of FIG. 2 in that the tilted state (as in the case for the CT device according to FIG. 1) is effected again by means of tilting the gantry 1. In order to enable a relative movement here as well between the gantry 1 and the support plate 7 in the direction of the system axis Z, the support plate 7 is synchronously adjusted in the direction of the longitudinal axis L relative to the pedestal 9 by means of the support part 10, and the pedestal 9 is adjusted in its height (indicated by the double arrow y) for performing a spiral scan. The two movements in the direction l and the y-direction ensue with speeds l and y, which have a constant relation to one another, this relation being selected such that the movement resulting from the movements in the direction l and the y-direction is linear and ensues in the z-direction, namely in the direction of the system axis Z.

Therefore, conventional methods for spiral interpolation and for eliminating ring artefacts can also be utilized in the exemplary embodiment according to FIG. 3. The embodiment according to FIG. 3 has the advantage that a patient lying on the support plate 7 can remain in a horizontal position, which is more comfortable.

In the exemplary embodiment according to FIG. 3, drives 11 and 12 are provided for generating the movements in the direction l and the y-direction. The drives 11 and 12 are preferably electromotors with appropriate gears (transmissions) that are switched downstream. The drives 11 and 12 are connected to a control unit 13, and an angle transmitter that is also connected to the control unit 13 supplies an electrical signal to the control unit 13, which corresponds to the adjusted inclination of the system axis Z relative to the longitudinal axis L. For performing a spiral scan, the control unit 13, which, for example, is a component of an overall device control (not shown in greater detail in FIG. 3) that controls the operation of the CT device according to FIG. 3, operates the drives 11 and 12 on the basis of the signals supplied by the angle transmitter such that a movement of the support plate 7 results in the z-direction. The vectorial addition of the corresponding speeds l, y, and z is shown in FIG. 3.

Figure 4:
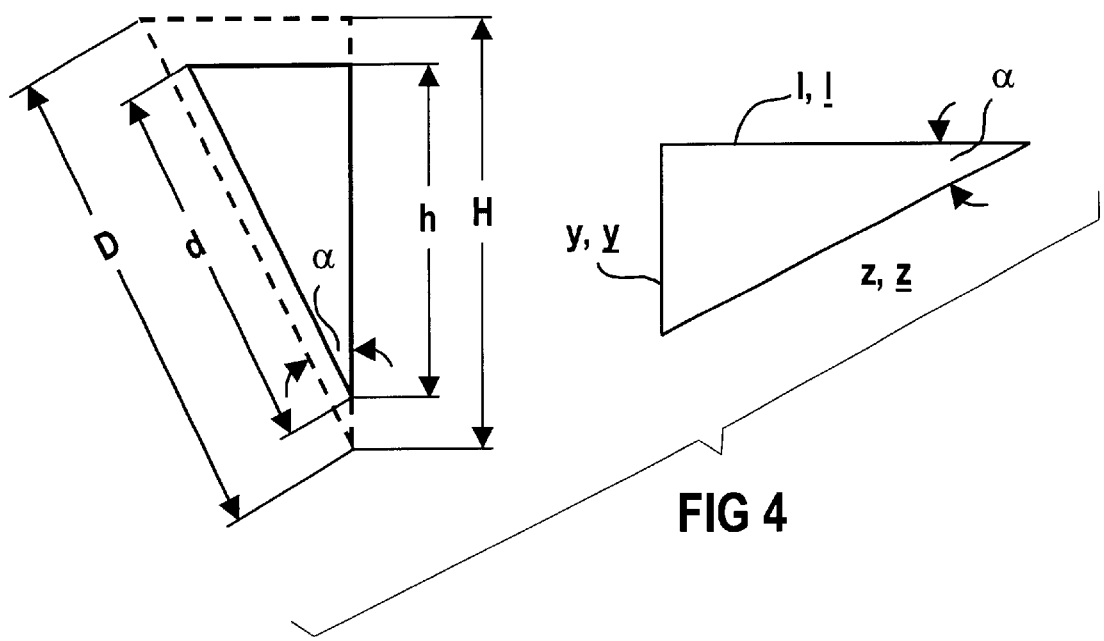
FIG. 4 is a diagram illustrating the geometrical relations on which the inventive CT devices according to FIGS. 2 and 3 are based.

In both exemplary embodiments, it must be taken into consideration that the movement of the support plate 7 in the direction of the system axis Z is limited due to the diameter of the measuring opening 2 (shown in FIG. 4).

For example, when the diameter of the measuring opening 2 is D=70 cm, and the diameter of the measuring field (normally the area that is concentrically arranged within the measuring opening, in which area examinations are possible) is d=50 cm and when the maximal tilt angle between system axis Z and longitudinal axis L of the bearing plate 7 is α=30°, a clearance height of the measuring opening 2 of H=D*cos 30°=60.6 cm remains and a utilizable height of the measuring field, with respect to imaging purposes, of h=d*cos 30°=43.3 cm. For example, when the support plate 7 is adjusted by z=10 cm in the direction of the system axis Z, the support plate 7 is displaced in the direction of its longitudinal axis L, namely in the l-direction, by l=z*cos 30°=8.66 cm and the distance between the bearing plate 7 and the uppermost point of the measuring field changes by y=z*sin 30°=5 cm in the vertical direction, namely in the y-direction. Given a displacement of the support plate 7 by z=23 cm in the direction of the system axis Z, the distance between the support plate 7 and the uppermost point of the measuring field therefore changes by y=z*sin 30°=11.5 cm, so that the smallest value of the height of the measuring field utilizable for imaging purposes is 43.3 cm−11.5 cm=31.8 cm.

When areas of the patient come to lie outside of the measuring field, which is normally smaller than the measuring opening 2, an image of high quality can still be generated using appropriate correction methods, such as the technique known as "obese correction", for example.

The above cited numerical values are valid for a relatively large tilt angle of 30°, which is only rarely required. Normally, smaller tilt angles are utilized, since they allow larger displacement paths of the support plate 7.

Small deviations of the direction of movement from the direction of the system axis Z are allowable in the context of the invention, since slight deviations do not lead to unacceptable image disturbances.

In the described exemplary embodiments, the relative movement between the gantry 1 and the support plate 7 is generated by displacing the support plate 7. In the context of the invention, however, it is also possible to leave the support plate 7 stationary and to displace the gantry 1 instead. Also, in the context of the invention, it is possible to generate the necessary relative movement by displacing not only the gantry 1 but also the support plate 7.

CT devices of the third generation have been described in the exemplary embodiments, i.e. the X-ray source 4 and the detectors rotate together around the system axis Z during the image generation. The invention also can be utilized with CT devices of the fourth generation, wherein only the X-ray source (or at least the focus thereof) rotates and cooperates with a fixed detector ring.

The above described exemplary embodiments relate to the medical application of inventive CT devices, however, the invention also can be employed outside of the medical field, for example, for baggage checks or material examinations.

I claim as my invention:

1. A computed tomography apparatus comprising:

a gantry;

an x-ray source having a focus from which an x-ray beam emanates and a radiation detector on which said x-ray beam is incident, said radiation detector having a plurality of rows of detector elements;

a patient support adapted to receive an examination subject thereon in said x-ray beam, said patient support having a longitudinal axis;

said gantry and said patient support being tiltable relative to each other into a tilted state wherein a system axis and said longitudinal axis are inclined relative to each other and wherein, in said tilted state, said patient support and said gantry are linearly adjustable relative to each other to generate a relative movement in the direction of said system axis between said gantry and said patient support; and at least said focus being displaceable around said system axis coordinated with said relative movement in the direction of said system axis between said gantry and said patient support, with said examination subject disposed in said x-ray beam, to conduct a spiral scan, and said radiation detector generating data from which tomograms of slices of an examination subject are computed which are inclined relative to said longitudinal axis of said patient support.

2. A computed tomography apparatus as claimed in claim 1 wherein, in said tilted state, said system axis proceeds substantially horizontally.

3. A computed tomography apparatus as claimed in claim 1 wherein, in said tilted state, said longitudinal axis proceeds substantially horizontally.

4. A computed tomography apparatus as claimed in claim 1 wherein, in said tilted state, only said patient support is linearly adjusted for generating said relative movement, said patient support being adjusted along said system axis.

5. A computer tomography apparatus as claimed in claim 4 wherein said patient support is linearly adjusted by a combination of movement along said longitudinal axis and movement in a direction perpendicular to said longitudinal axis.

* * * * *